(12) United States Patent
Lieberman et al.

(10) Patent No.: US 7,748,385 B2
(45) Date of Patent: Jul. 6, 2010

(54) VALVED HOLDING CHAMBER FOR USE WITH AN AEROSOL MEDICATION DELIVERY SYSTEM

(75) Inventors: Eric Lieberman, Orange, NJ (US); Dirk Von Hollen, Clark, NJ (US)

(73) Assignee: RIC Investments, Inc, Wilmington, DE (US)

( * ) Notice: Subject to any disclaimer, the term of this patent is extended or adjusted under 35 U.S.C. 154(b) by 1020 days.

(21) Appl. No.: 10/848,213

(22) Filed: May 18, 2004

(65) Prior Publication Data

US 2004/0231665 A1 Nov. 25, 2004

Related U.S. Application Data

(60) Provisional application No. 60/472,856, filed on May 23, 2003.

(51) Int. Cl.
*A61M 16/20* (2006.01)
*A62B 18/10* (2006.01)

(52) U.S. Cl. .............................. 128/207.12; 128/203.11; 128/205.24; 128/206.15; 128/207.16; 137/846; 137/859; 137/512.3; 137/102

(58) Field of Classification Search ............ 128/205.24, 128/200.14, 200.23, 203.12, 203.11, 203.15, 128/203.29, 202.28, 202.29, 207.12, 207.16, 128/202.08; 137/846, 859, 512.3, 102

See application file for complete search history.

(56) References Cited

U.S. PATENT DOCUMENTS

| | | | | |
|---|---|---|---|---|
| 2,292,373 A | * | 8/1942 | Groeniger | 137/218 |
| 2,674,318 A | * | 4/1954 | Sutliff | 166/165 |
| 4,470,412 A | | 9/1984 | Nowacki et al. | |
| 4,622,964 A | * | 11/1986 | Flynn | 128/205.24 |

(Continued)

FOREIGN PATENT DOCUMENTS

WO    WO 03/092777    * 11/2003

*Primary Examiner*—Justine R Yu
*Assistant Examiner*—Clinton Ostrup
(74) *Attorney, Agent, or Firm*—Timothy A. Nathan (57) ABSTRACT

The present invention pertains to a valved holding chamber suitable for use in an aerosol medication delivery system. The valved holding chamber includes a housing and a mouthpiece coupled to the housing. A one-way valve assembly is coupled to the housing, the mouthpiece, or both so that fluid flows in a first direction from the housing to the mouthpiece passes through the valve assembly but does not pass back into the housing. The valve assembly includes a conical flange disposed such that the conical flange tapers in the first direction to smooth the fluid flow in the first direction toward the patient. In a further embodiment, the mouthpiece includes an exhaust port defined in a conical collar portion of the mouthpiece, and an exhaust valve element is disposed over the exhaust port to provide a one-way flow of fluid from within the mouthpiece to ambient atmosphere via the exhaust port.

24 Claims, 9 Drawing Sheets

U.S. PATENT DOCUMENTS

| | | | |
|---|---|---|---|
| 4,809,692 A | 3/1989 | Nowacki et al. | |
| 4,832,015 A | 5/1989 | Nowacki et al. | |
| 5,005,568 A * | 4/1991 | Loescher et al. | 128/202.28 |
| 5,012,803 A | 5/1991 | Foley et al. | |
| 5,042,467 A | 8/1991 | Foley | |
| 5,385,140 A | 1/1995 | Smith | |
| 5,503,140 A * | 4/1996 | Winefordner et al. | 128/200.29 |
| 5,645,049 A * | 7/1997 | Foley et al. | 128/203.29 |
| 5,816,240 A * | 10/1998 | Komesaroff | 128/200.23 |
| 5,848,588 A | 12/1998 | Foley et al. | |
| 5,881,718 A * | 3/1999 | Mortensen et al. | 128/203.11 |
| 6,026,807 A * | 2/2000 | Puderbaugh et al. | 128/200.23 |
| 6,039,042 A * | 3/2000 | Sladek | 128/200.23 |
| 6,557,549 B2 | 5/2003 | Schmidt et al. | |
| 7,013,896 B2 * | 3/2006 | Schmidt | 128/206.15 |
| 7,028,707 B2 * | 4/2006 | Corbeil et al. | 137/493 |
| 2003/0205226 A1 * | 11/2003 | Gallem et al. | 128/200.14 |
| 2003/0234015 A1 * | 12/2003 | Bruce et al. | 128/200.23 |

* cited by examiner

VALVED HOLDING CHAMBER FOR USE WITH AN AEROSOL MEDICATION DELIVERY SYSTEM

CROSS-REFERENCE TO RELATED APPLICATIONS

This application claims priority under 35 U.S.C. §119(e) from provisional U.S. patent application No. 60/472,856 filed May 23, 2003 the contents of which are incorporated herein by reference.

BACKGROUND OF THE INVENTION

1. Field of the Invention

The present invention pertains to an aerosol medication delivery system, and, in particular, to a valved holding chamber for use in an aerosol medication delivery system that maximizes delivery of the aerosol medication to a patient.

2. Description of the Related Art

It is well known to deliver a medication to a patient's respiratory system to treat a medical condition using an aerosol medication delivery system. For example, a patient suffering from an acute asthmatic attack may use an aerosol medication delivery system to deliver a bronchodilator, such as albuterol (salbutamol), in the form of a fine mist to the patient's respiratory system.

A conventional aerosol medication delivery system often consists of a metered dose inhaler ("MDI") and a spacer. The MDI, also known simply as an "inhaler", includes a canister or nebulizer that contains the medication under pressure and a canister holder, which is typically "L" shaped. Although it is common for a patient to use the canister holder as a mouthpiece for receiving the aerosolized medication into their airway directly from the aerosol dispensing leg of the canister holder, this configuration may not optimize the mixing of the medication with the air because the aerosolized medication is injected directly into the airway. Without adequate mixing of the drug with the air, the medication may not be inhaled into the patient's lungs where it is effective, but may form as droplets that are deposited in the patient's mouth and swallowed without the desired medicinal effect.

To enhance mixing of the medication with air, it is known to provide a spacer that attaches to the aerosol dispensing end of the canister holder. The spacer, which is typically a small hollow cylinder with a one-way valve at the downstream end, receives the aerosol from the canister and allows it to form into a fine mist for inhalation into the airway of the patient. It is also known to provide a mask at the end of the spacer opposite the MDI so that the patient can breath through his or her mouth to receive the medication. Examples of conventional spacers and associated components are shown in U.S. Pat. Nos. 4,470,412; 4,809,692; and 4,832,015 all to Nowacki et al.; U.S. Pat. No. 5,012,803 to Foley et al.; U.S. Pat. No. 5,042,467 to Foley; U.S. Pat. No. 5,385,140 to Smith, U.S. Pat. No. 5,848,599 to Foley et al., and U.S. Pat. No. 6,557,549 to Schmidt et al.

While the spacers described in these patents improve mixing of the medication with air, still further improvements in this mixing is desirable. Furthermore, the devices described in these patents are relatively complicated, especially in the valves used to control the flow of the drug/air mixture and patient exhalation. The more complicated the system, the more prone they are to failure or degradation in performance, for example due to clogging, and the more difficult it is to disassemble, clean, and reassemble the system correctly and quickly.

SUMMARY OF THE INVENTION

Accordingly, it is an object of the present invention to provide an aerosol delivery system that overcomes the shortcomings of conventional aerosol delivery systems. This object is achieved according to one embodiment of the present invention by providing an aerosol delivery system that includes a canister adapted to dispense a medicine, a canister holder adapted to couple to the canister, and a valved holding chamber that is adapted to be coupled to an end of the canister holder so that medicine or other fluid dispensed from the canister via the canister holder enters the valved holding chamber. The valved holding chamber includes a housing having a first end portion, a second end portion, and a chamber defined in the housing. A first chamber opening is defined in the first end portion and a second chamber opening is defined in the second end portion of the housing both of which provide access to the chamber. A mouthpiece is coupled to the first end portion of the housing, and a valve assembly is coupled to the housing, the mouthpiece, or both. The valve assembly is coupled to these elements such that fluid flow in a first direction from the housing to the mouthpiece passes through the valve assembly. More specifically, the valve assembly includes a conical flange having a first end coupled to the housing, the mouthpiece, or both such that the conical flange tapers in the first direction. A one-way valve element is disposed at the second end of the conical flange to allow fluid to flow from the chamber to the mouthpiece, i.e., in the first direction, but prevent fluid flow in an opposite direction. A valved holding chamber of such configuration provides improved medication/air mixing because the unobstructed flow of gas from the chamber into the valve assembly and the conical shape of the valve assembly provides a smooth transition, in terms of fluid flow, from the chamber to the one-way valve element.

A further embodiment of the present invention provides a simple and effective technique for preventing fluid flow back into the chamber, which is especially likely as the patient exhales into the mouthpiece, by providing an exhaust port in a conical collar portion of the mouthpiece and an exhaust valve element disposed over the exhaust port. The exhaust valve element is preferably selectively attachable to the exterior of the mouthpiece so that the exhaust valve element and the mouthpiece can be easily separated, cleaned, and reassembled.

These and other objects, features and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention. As used in the specification and in the claims, the singular form of "a", "an", and "the" include plural referents unless the context clearly dictates otherwise.

DETAILED DESCRIPTION OF THE PRESENTLY PREFERRED EMBODIMENTS OF THE INVENTION

Figure 1:
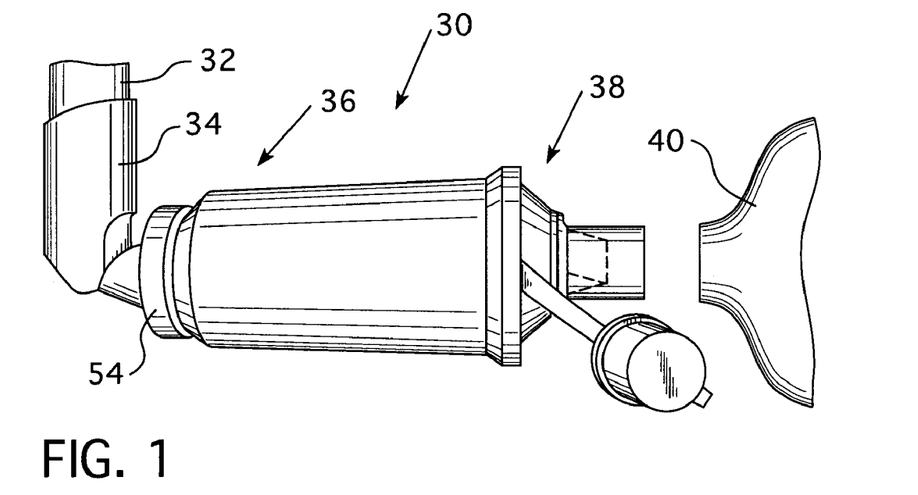
FIG. 1 is a side view of an aerosol medication delivery system including a valved holding chamber according to the principles of the present invention.

FIG. 1 is a side view of an exemplary embodiment of an aerosol medication delivery system 30 according to the principles of the present invention. Aerosol medication delivery system 30 includes a canister 32 adapted to dispense a medicine, a canister holder 34 that holds the canister, and a valved holding chamber 36 that attaches to the fluid dispensing end of the canister holder. The present invention contemplates that canister 32 and canister holder 34 are conventional devices. The unique features of the present invention are believed to reside in the valved holding chamber that selectively couples to an end of the canister holder. A mouthpiece assembly 38 provided at a first end of valved holding chamber 36 communicates with an airway of a patient (not shown), either directly, by having the patient place his or her lips on the mouthpiece, or indirectly, by attaching a mask 40 to the mouthpiece. Details of valved holding chamber 36 are discussed below the reference to FIGS. 2-9.

Figure 2:
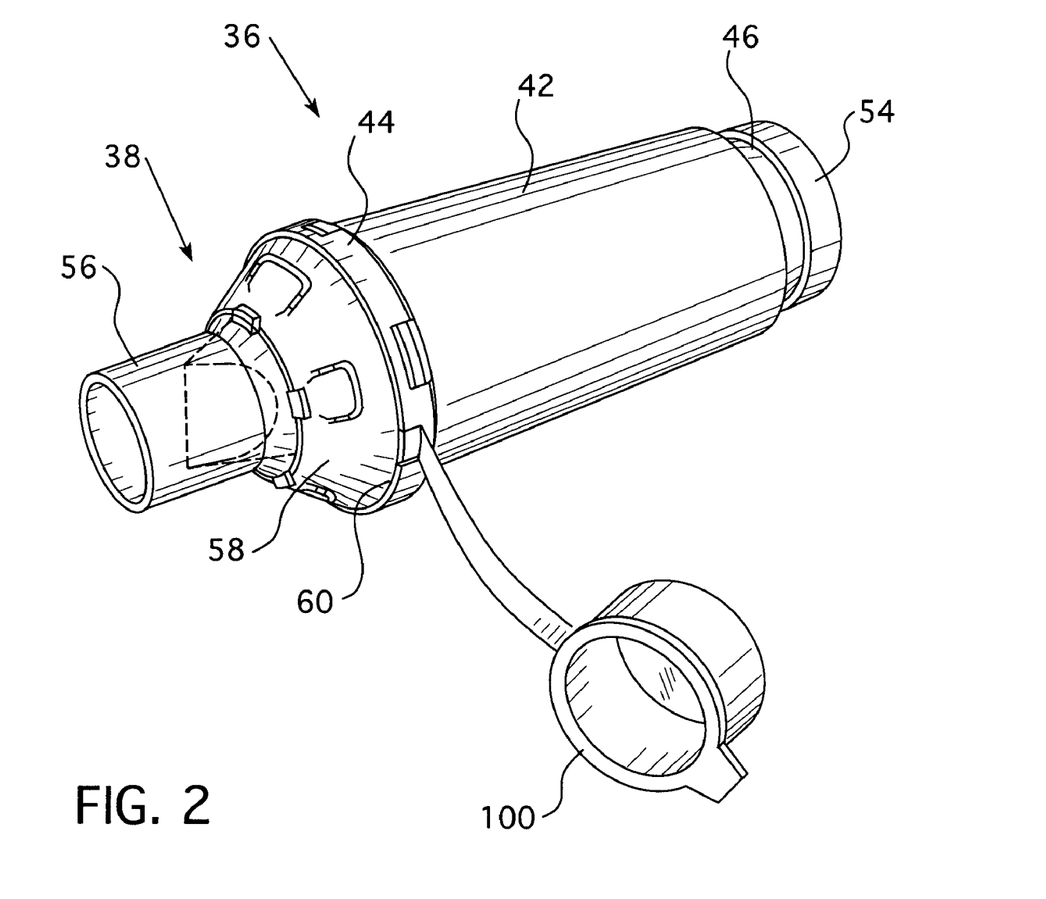
FIG. 2 is a perspective view of the valved holding chamber of FIG. 1.
Figure 3:
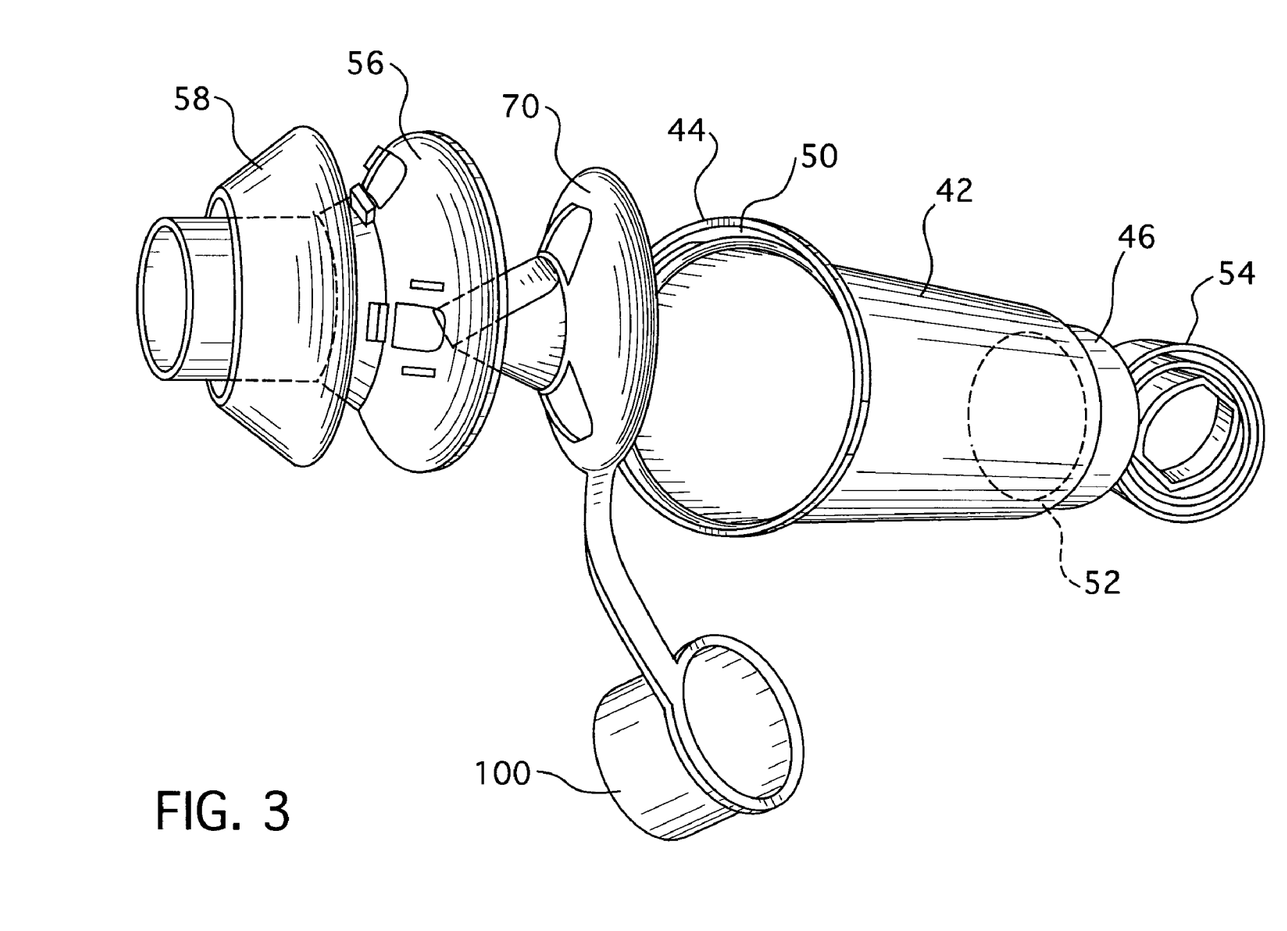
FIG. 3 is an exploded view of the valved holding chamber of FIG. 1.
Figure 4:
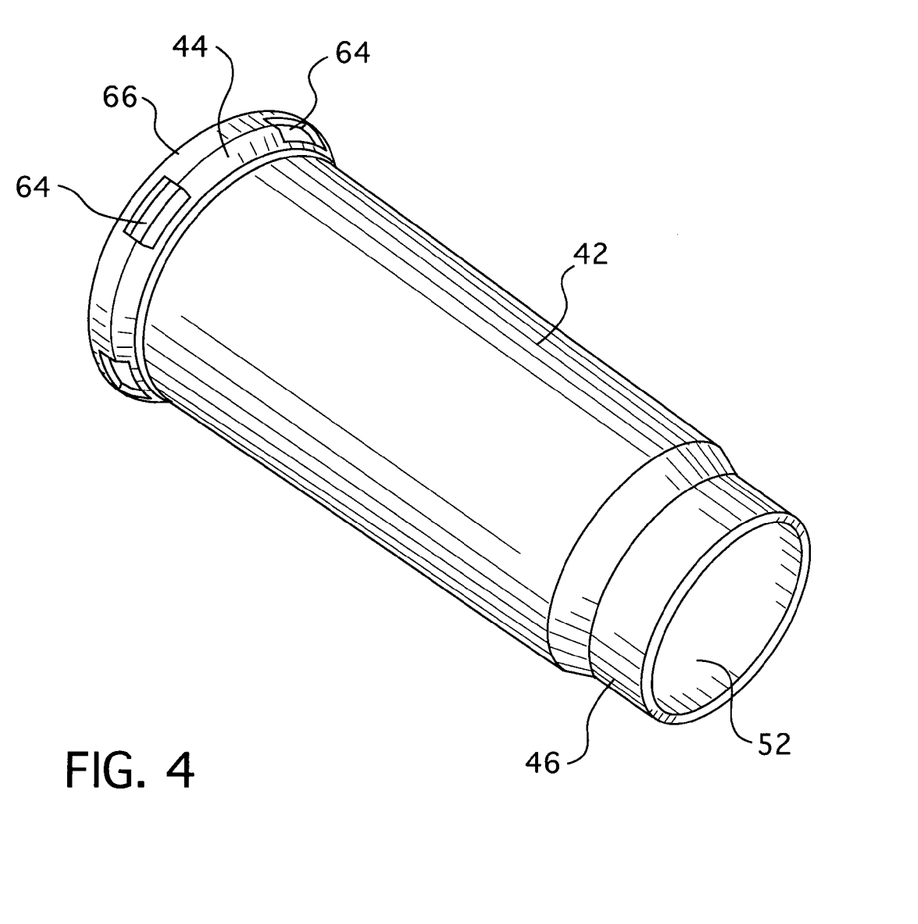
FIG. 4 is a perspective view of the housing used in the valved holding chamber of FIG. 1.

Valved holding chamber 36 includes a housing 42 having a first end portion 44, a second end portion 46, and a chamber 48 defined in the housing. A first chamber opening 50 is defined in the first end portion and a second chamber opening 52 is defined in the second end portion of housing 42 to allow fluid to enter and exit the chamber. Mouthpiece assembly 38 is coupled to first end portion 44 of housing 42 so that fluid, which includes a nebulized medication, communicates from chamber 48 to the mouthpiece assembly through first chamber opening 50. Second chamber opening 52 allows fluid to be injected from canister 32 via canister holder 34 into chamber 48. The present invention contemplates providing an MDI adapter 54 at second end portion 46 to provide a sealed engagement between the fluid dispending end of canister holder 34 and housing 42.

Mouthpiece assembly 38 includes a mouthpiece member 56 and an exhaust valve ring 58, the purpose of which is discussed in detail below. In the illustrated exemplary embodiment, a first end portion 60 of mouthpiece member 56 is maintained in an engaged relation with first end portion 44 of housing 42 due to an engagement between ridges 62, which are provided at an edge of first end portion 60, and slots 64, which are defined at corresponding location around the perimeter in a retaining ring 66 disposed at the first end portion of the housing.

It is to be understood that the present invention contemplates other techniques for attaching mouthpiece assembly 38 to housing 42. For example, the ridge and slot arrangement can be reversed, with the slots being defined in the mouthpiece member and the ridges provided in the retaining ring. Of course, other techniques, such as a male/female snap fit assembly, tongue and groove assembly, or a simple pressure fit frictional engagement can be provided around the perimeter of the mouthpiece and housing to create a positive engagement between these two elements. Regardless of the technique used to join the mouthpiece to the housing, it is preferable that these elements be secured together securely so that they cannot be easily separated from one another. Of course, the present invention also contemplate the opposite—that the components of the valved holding chamber are configured and arranged so as to be easily disassembled and reassembled, for example, for cleaning purposes.

Figure 5:
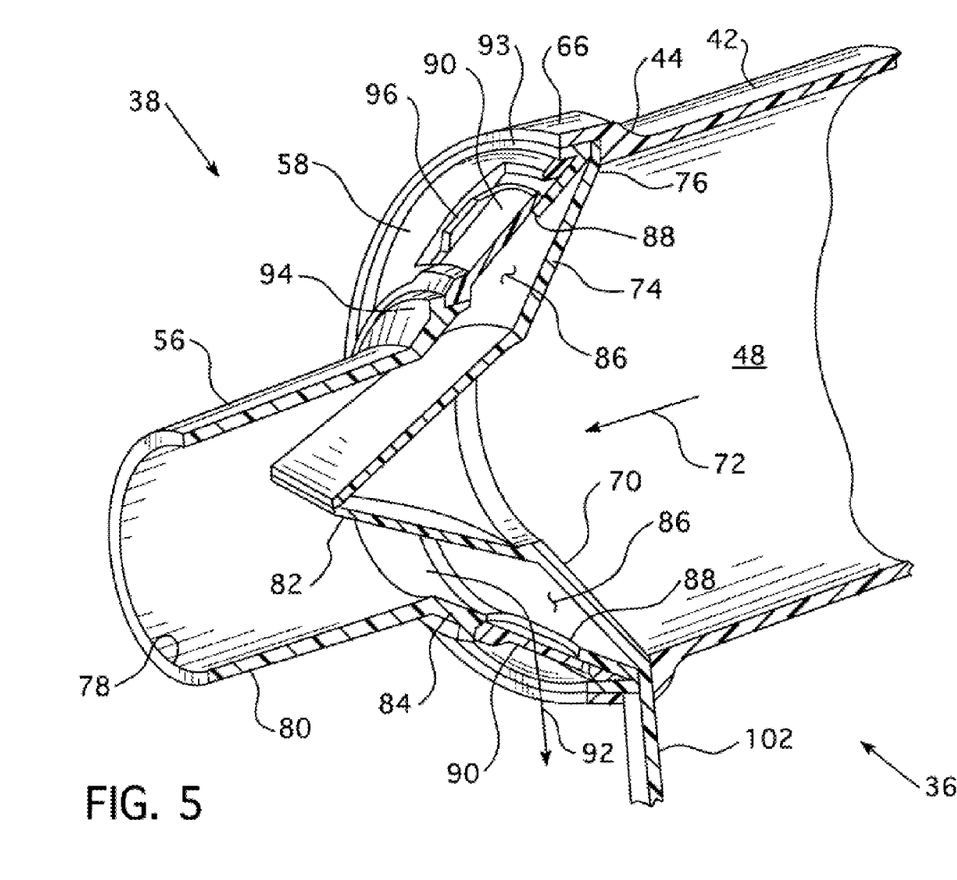
FIG. 5 is a perspective sectional view of the portion of the valved holding chamber that includes the mouthpiece assembly and valve assembly.
Figure 6A:
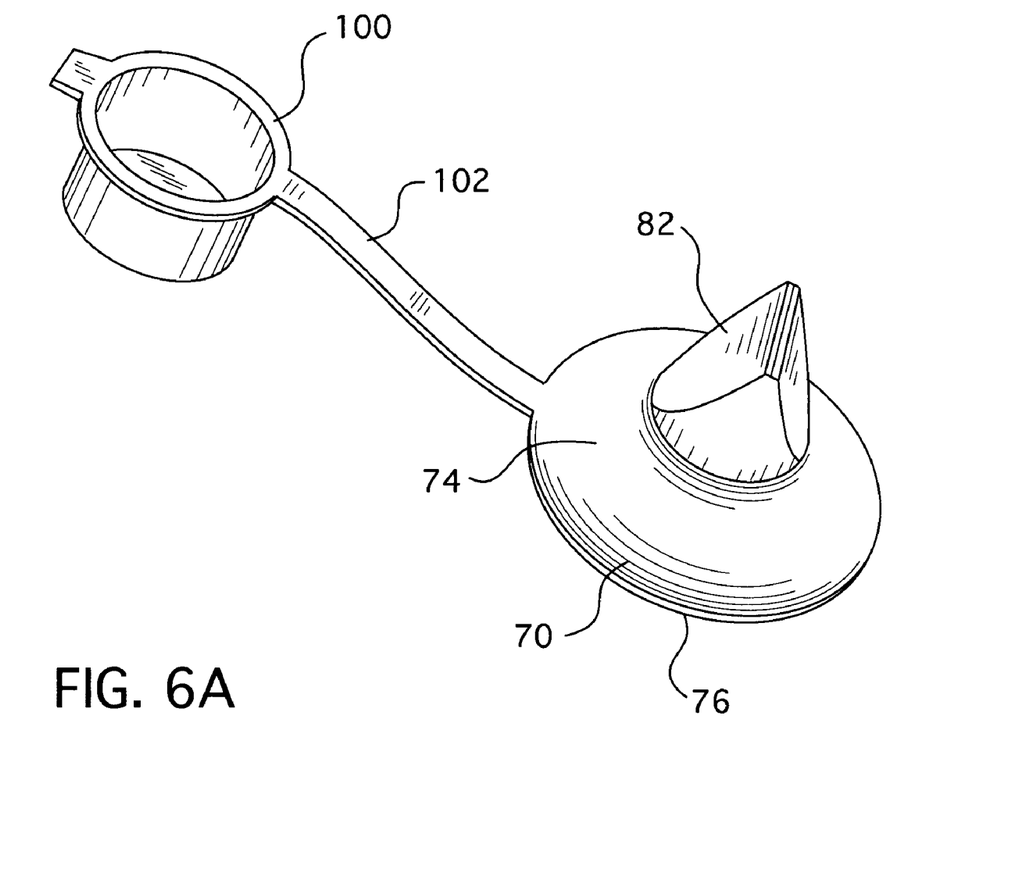
FIG. 6A is a perspective view of a first embodiment of the valve assembly including a duck-bill valve.
Figure 6B:
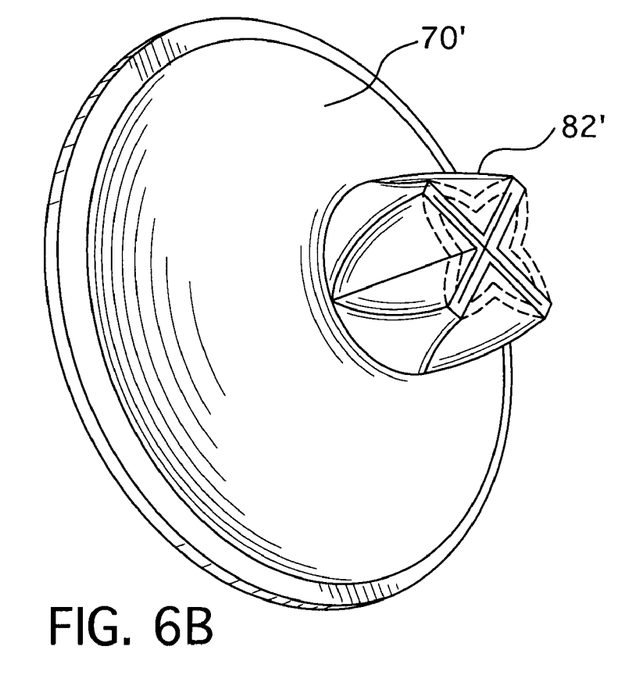
FIG. 6B is a perspective view of a second embodiment of the valve assembly including a cross-slit valve.

Valved holding chamber 36 also includes a valve assembly 70 that allows a one-way flow of fluid in a first direction from housing 42 to mouthpiece assembly 38, as indicated by arrow 72 in FIG. 5, so that the flow of fluid passes through the valve assembly. Valve assembly 70 includes a conical flange 74 having a first end portion 76 that is coupled to first end portion 44 of housing 42 and to first end portion 60 of mouthpiece assembly 38. More specifically, the first end portion of conical flange 74 is sandwiched between housing 42 and first end portion 60 of mouthpiece member 56. It should be noted that the present invention contemplates that the conical flange can be coupled only to the mouthpiece or only to the housing using any conventional fastening technique.

Conical flange 74 is arranged such that the flange tapers in first direction corresponding to that indicated by arrow 72 so that the cross-sectional area of the flange reduces in a direction toward an opening 78 defined in a second end portion 80 of mouthpiece member 56. This linear taper provides a smooth transition for the flow of fluid from chamber 36 into an interior 66 of mouthpiece 38. The smooth transition decreases the impact of the medicine/air mixture on the valve assembly that tends to occur in conventional spacers, which decreases the amount of available respirable drug to the patient. According to an embodiment of the invention, no portion of the valved holding chamber 36 downstream of the housing 42 intersects the fluid flow path perpendicularly relative to the longitudinal axis of the housing 42.

A one-way valve element 82 is disposed at a second end portion of conical flange 74. One-way valve element 82 allows the user to draw the air/medication mixture from chamber 48 into their airway during inhalation, and prevents the patient's exhalation from entering the chamber as the user exhales into mouthpiece assembly 38. In one embodiment of the present invention, one-way valve element 82 is a duck-bill valve. See FIG. 6A. In another embodiment of the present invention, valve assembly 70' has a one-way valve element 82' which is a cross-slit valve. See FIG. 6B.

In the illustrated embodiments of the present, valve assembly 70, and especially conical flange 74, is configured and arranged to have a shape that substantially matches a shape of a conical portion 84 of mouthpiece member 56. In addition, conical flange 74 is spaced apart from conical portion 84 so that a gap 86 is provided between conical flange 74 and an interior wall of mouthpiece member 56.

To allow the user's exhaled gases to pass from within mouthpiece assembly 38 to the ambient atmosphere, mouthpiece member 56 includes an exhaust port 88 defined in conical collar portion 84. It should be noted that more than one exhaust port can be provided in conical collar portion 84. For example, FIG. 5 shows two exhaust ports provided on opposite sides of mouthpiece member 56.

An exhaust valve element 90 is disposed over exhaust port 88 such that fluid flows only in a direction as indicated by arrow 92. That is, the patient's exhaled gas urge exhaust valve element 90 off of the conical collar portion of the mouthpiece member thereby unblocking exhaust port 88. Exhaust valve element 90 is biased to remain in the closed position shown, for example, in FIG. 5, so that during inhalation, the exhaust valve element prevents the ambient gas from entering the mouthpiece assembly. Thus, exhaust port 88 in combination with exhaust valve element 90 forms a one-way exhaust valve allowing fluid to pass from within an area corresponding to gap 86 within mouthpiece assembly 30 to the ambient atmosphere during exhalation, while prevent the ambient gas from entering the mouthpiece during inhalation.

Figure 7:
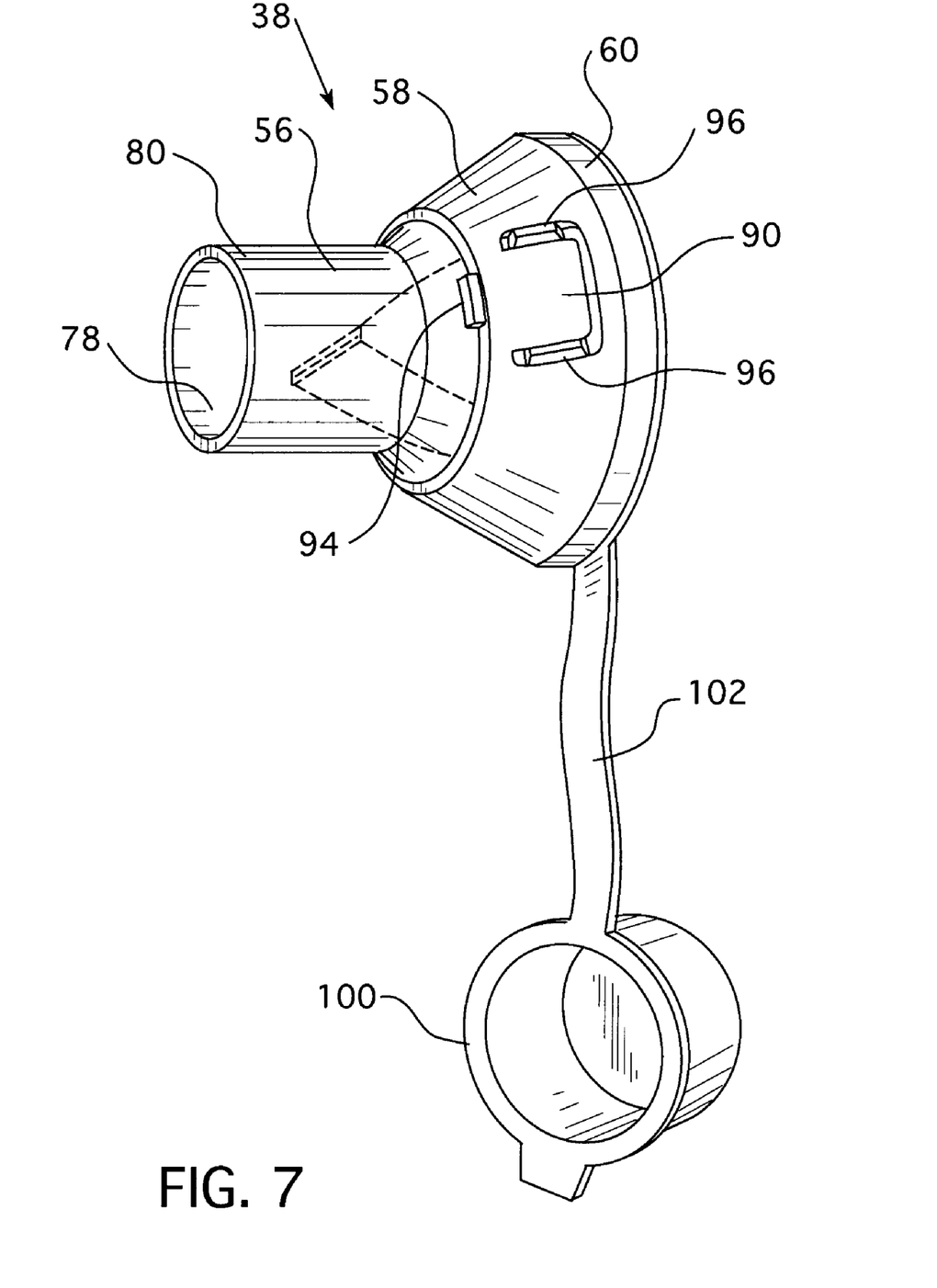
FIG. 7 is perspective view of the mouthpiece assembly for the valved holding chamber.
Figure 8:
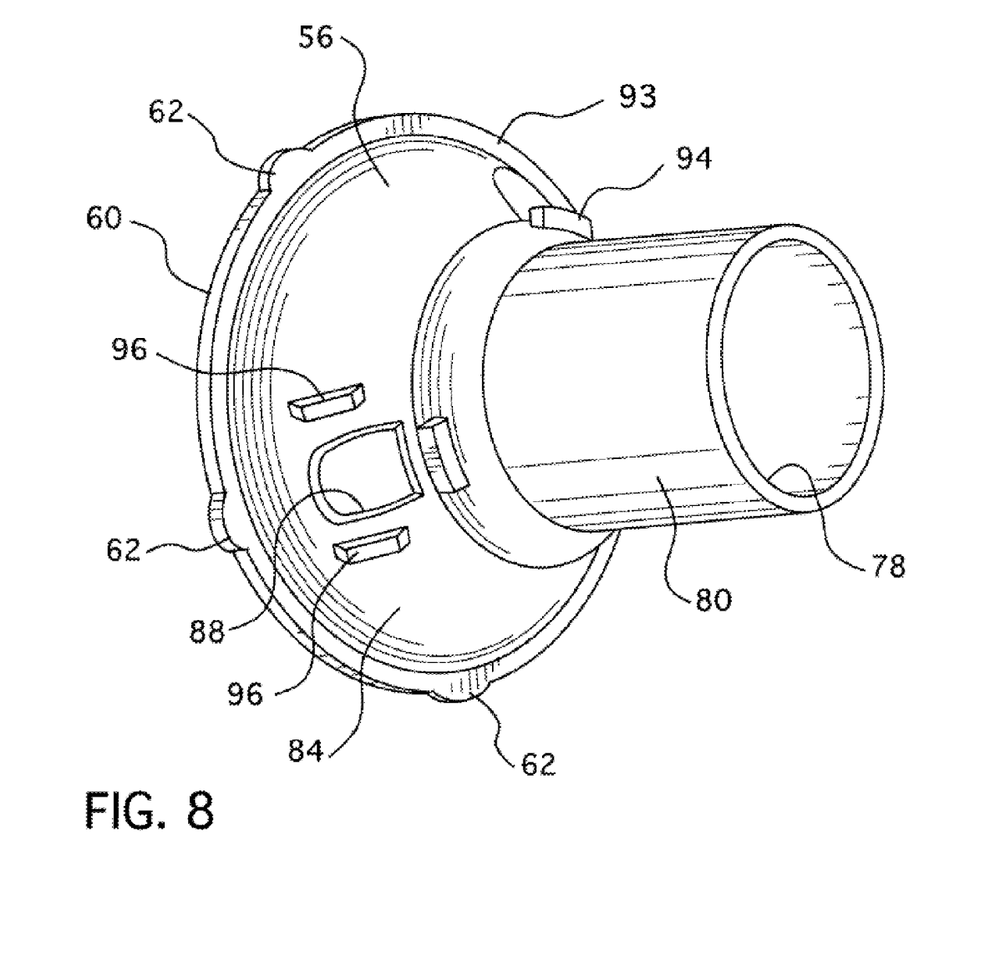
FIG. 8 is a perspective view of the mouthpiece member in the mouthpiece assembly of FIG. 7.
Figure 9:
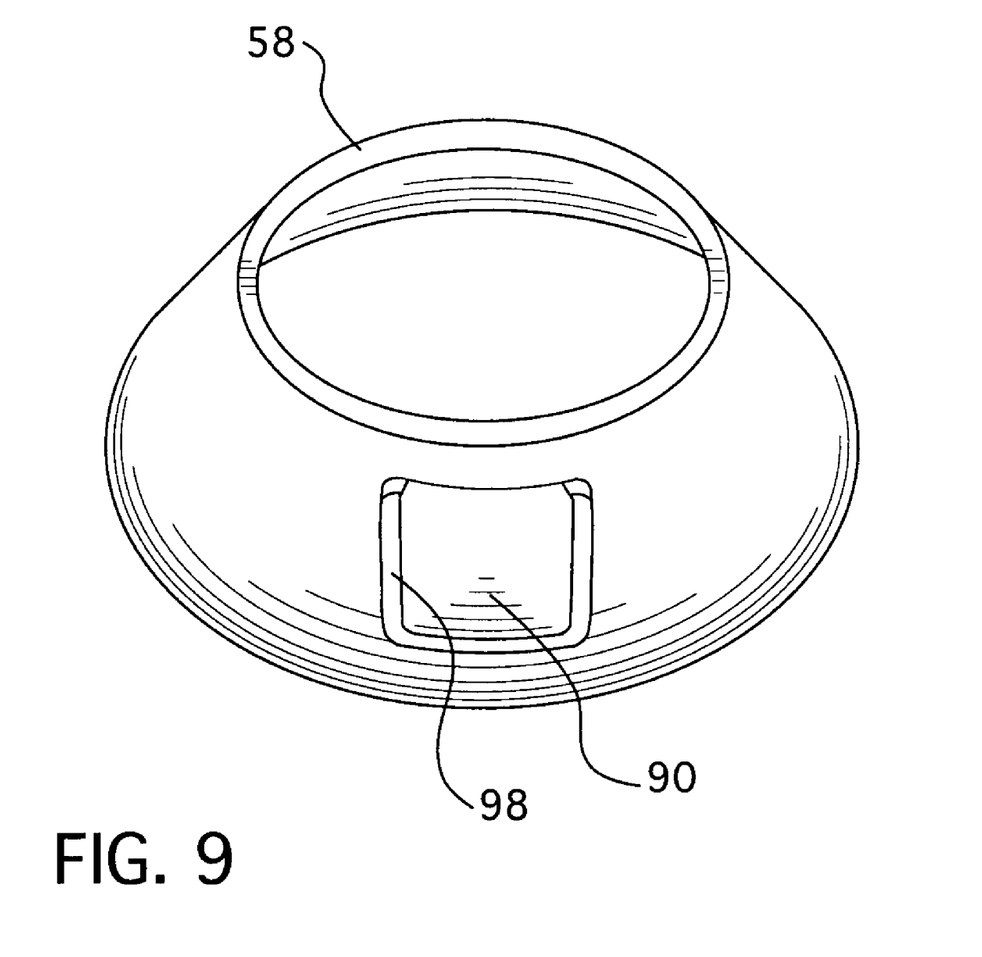
FIG. 9 is a perspective view of an exhaust valve ring that couples to the mouthpiece member in the mouthpiece assembly of FIG. 7.

Exhaust valve element 90 is preferably attached to mouthpiece member 56 by means of exhaust valve ring 58, which is adapted to be disposed over conical collar portion 84 of the mouthpiece member. More specifically, exhaust valve ring 58 slides over conical collar portion 84 until the exhaust valve ring is seated between a flange 93 provided on first end portion 54 of mouthpiece member 56 and a retaining member 94. In the illustrated exemplary embodiment, flange 93 is provided around first end portion 60. It is to be understood, however, that the flange need not be provided around the entire perimeter of the mouthpiece member and multiple retaining members 94 can be provided. The present invention also contemplates providing other techniques for securing exhaust valve ring 58 to mouthpiece member 56. For example, the exhaust valve ring can be disposed in a channel defined around the perimeter of the mouthpiece member.

Exhaust valve ring 58 is prevented from rotating with respect to mouthpiece member 56 by providing guide members 96 that engage the sides of the opening defining exhaust valve when the exhaust valve ring is properly positioned on the mouthpiece member. Thus, guide members 56 and a gap 98 between exhaust valve element 90 and the remaining portion of the exhaust valve ring effectively form a slot and key that prevents rotation of the exhaust valve ring and also serves as a guide to ensure that exhaust valve element 90 is properly propositioned over an associated exhaust port 88.

Valve assembly 70 is preferably formed from a unitary piece of material so that conical flange 74 and exhaust valve element 90 are integrally formed. For example the present invention contemplates forming valve assembly from silicone. Exhaust valve ring 58, including exhaust valve element 90, are also preferably formed form this material. The present invention contemplates forming housing 46 and mouthpiece member 56 from the same type of material, such as polyethylene terephthalate (PET).

A further embodiment of the present invention contemplates providing a cap 100 that selectively closes opening 78 of mouthpiece member 56. Cap 100 is preferably coupled to duckbill valve 70 via a tether 102. In a presently preferred embodiment, cap 100 and tether 102 are integrally formed with valve assembly 70. This provides an advantage in that attaching the valve assembly to the valve holding chamber provides an automatic attachment of the cap to the spacer and reduces the number of parts for the overall system.

The present invention also contemplates controlling the pressure need to open exhaust port 88 by controlling the biasing force that urges exhaust valve element 90 into the closed position over exhaust port 88. For example, different exhaust valve rings that have different biasing forces for the exhaust valve element can be used on the same mouthpiece. Thus, the present invention is capable of providing an form of positive expiration therapy depending on which closing biasing force is applied to exhaust valve element 90.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims.

What is claimed is:

1. A valved holding chamber comprising:
   (a) a housing having a first end portion, a second end portion, and a chamber defined in the housing, wherein a first chamber opening is defined in the first end portion and a second chamber opening is defined in the second end portion;
   (b) a mouthpiece having a first end portion and a second end portion, the first end portion of the mouthpiece is coupled to the first end portion of the housing; and
   (c) a valve assembly operatively coupled to the first end portion of the housing or the first end portion of mouthpiece such that fluid flow in a first direction from the housing to the mouthpiece passes through the valve assembly defining a fluid flow path, wherein the valve assembly comprises:
   (1) a conical flange having a first end portion and a second end portion, the first end portion of the conical flange is operatively coupled to the housing, or the mouthpiece, wherein the conical flange is disposed such that the conical flange tapers inwardly along a first direction extending from the first end portion of the conical flange to the second end portion of the conical flange, wherein the first end portion of the conical flange abuts an interior wall of the chamber, and
   (2) a one-way valve element disposed at the second end portion of the conical flange, the one-way valve element is integral with the conical flange, the one-way valve element is movable to selectively permit or impede fluid flow, wherein no portion of the valved holding chamber downstream of the housing intersects the fluid flow path perpendicularly relative to the longitudinal axis of the housing.

2. The valved holding chamber of claim 1, wherein the first end portion of the mouthpiece includes a conical collar.

3. The valved holding chamber of claim 2, further comprising an exhaust port defined in the conical collar, and an exhaust valve element disposed over the exhaust port.

4. The valved holding chamber of claim 1, further comprising a mask attached to the second end portion of the mouthpiece.

5. The valved holding chamber of claim 1, where the one-way valve element is a duck-bill valve or a cross-slit valve.

6. The valved holding chamber of claim 1, wherein the first end portion of the housing and the first end portion of the mouthpiece are connected to each other such that first end portion of the conical flange is sandwiched between the first end portion of the housing and the first end portion of the mouthpiece.

7. The valved holding chamber of claim 1, wherein the valve assembly has a shape that substantially matches a shape of the mouthpiece.

8. The valved holding chamber of claim 1, wherein the housing and the mouthpiece are defined from a rigid material and the valve assembly is defined from a unitary piece of non-rigid material.

9. The valved holding chamber of claim 1, wherein the valve assembly is integrally formed as a unitary, non-rigid piece of material.

10. A valved holding chamber comprising:
(a) a housing having a first end portion, a second end portion, and a chamber defined in the housing, wherein a first chamber opening is defined in the first end portion and a second chamber opening is defined in the second end portion;
(b) a mouthpiece having a first end portion and a second end portion, the first end portion of the mouthpiece is coupled to the first end portion of the housing; and
(c) a valve assembly operatively coupled to the first end portion of the housing or the first end portion of mouthpiece such that fluid flow in a first direction from the housing to the mouthpiece passes through the valve assembly defining a fluid flow path, wherein the valve assembly comprises:
(1) a conical flange having a first end portion and a second end portion, the first end portion of the conical flange is operatively coupled to the housing, or the mouthpiece, wherein the conical flange is disposed such that the conical flange tapers inwardly along a first direction extending from the first end portion of the conical flange to the second end portion of the conical flange, and
(2) a one-way valve element disposed at the second end portion of the conical flange, the one-way valve element is integral with the conical flange, the one-way valve element is movable to selectively permit or impede fluid flow, wherein no portion of the valved holding chamber downstream of the housing intersects the fluid flow path perpendicularly relative to the longitudinal axis of the housing, wherein the first end portion of the mouthpiece includes a conical collar, wherein said valved holding chamber further comprises an exhaust port defined in the conical collar, and an exhaust valve ring disposed over the conical collar, wherein the exhaust valve ring comprises an exhaust valve element disposed over the exhaust port, and wherein the exhaust valve ring maintains the exhaust valve element on the conical collar.

11. A valved holding chamber comprising:
(a) a housing having a first end portion, a second end portion, and a chamber defined in the housing, wherein a first chamber opening is defined in the first end portion and a second chamber opening is defined in the second end portion;
(b) a mouthpiece having a first end portion and a second end portion, the first end portion of the mouthpiece is coupled to the first end portion of the housing;
(c) a valve assembly operatively coupled to the first end portion of the housing or the first end portion of mouthpiece such that fluid flow in a first direction from the housing to the mouthpiece passes through the valve assembly defining a fluid flow path, wherein the valve assembly comprises:
(1) a conical flange having a first end portion and a second end portion, the first end portion of the conical flange is operatively coupled to the housing, or the mouthpiece, wherein the conical flange is disposed such that the conical flange tapers inwardly along a first direction extending from the first end portion of the conical flange to the second end portion of the conical flange, and
(2) a one-way valve element disposed at the second end portion of the conical flange, the one-way valve element is integral with the conical flange, the one-way valve element is movable to selectively permit or impede fluid flow, wherein no portion of the valved holding chamber downstream of the housing intersects the fluid flow path perpendicularly relative to the longitudinal axis of the housing;
(d) a cap adapted to selectively close the second end portion of the mouthpiece; and
(e) a tether coupling the cap to the valve assembly.

12. An aerosol medication delivery system comprising:
(a) a canister adapted to dispense a medicine;
(b) a canister holder adapted to couple to the canister; and
(c) a valved holding chamber coupled to an end of the canister holder comprising:
(1) a housing having a first end portion, a second end portion coupled to an end portion of the canister holder, and a chamber defined in the housing, wherein a first chamber opening is defined in the first end portion and a second chamber opening is defined in the second end portion;
(2) a mouthpiece having a first end portion and a second end portion, the first end portion of the mouthpiece is coupled to the first end portion of the housing; and
(3) a valve assembly operatively coupled to the first end portion of the housing or the first end portion of the mouthpiece such that fluid flow in a first direction from the housing to the mouthpiece passes through the valve assembly defining a fluid flow path, wherein the valve assembly comprises:
(i) a conical flange having a first end portion, the first end portion of the conical flange is operatively coupled to the housing, or the mouthpiece; and a second end portion of the conical flange, wherein the conical flange is disposed such that the conical flange tapers inwardly along a first direction extending from the first end portion of the conical flange towards the second end portion of the conical flange, and
(ii) a one-way valve element disposed as the second end portion of the conical flange, the one-way valve element is integral with the conical flange, the one-way valve element is movable to selectively permit or impede fluid flow, wherein no portion of the valved holding chamber downstream of the housing intersect the fluid flow path perpendicularly relative to the longitudinal axis of the housing;
(d) a cap adapted to selectively close the second end portion of the mouthpiece; and
(e) a tether coupling the cap to the valve assembly.

13. The system of claim 12, wherein the first end portion of the mouthpiece includes a conical collar.

14. The system of claim 13, further comprising an exhaust port defined in the conical collar, and an exhaust valve element disposed over the exhaust port.

15. The system of claim 12, further comprising a mask attached to the second end of the mouthpiece.

16. The system of claim 12, where the one-way valve element is a duck-bill valve or a cross-slit valve.

17. The system of claim 12, wherein the first end portion of the housing and the first end portion of the mouthpiece are connected to each other such that first end portion of the conical flange is sandwiched between the first end portion of the housing and the first end portion of the mouthpiece.

18. The of claim 12, wherein the valve assembly has a shape that substantially matches a shape of the mouthpiece.

19. The system of claim 12, wherein the housing and the mouthpiece are defined by a rigid material and the valve assembly is defined from a unitary piece of non-rigid material.

20. The system of claim 12, wherein the valve assembly is integrally formed as a unitary, non-rigid piece of material.

21. An aerosol medication delivery system comprising:
(a) a canister adapted to dispense a medicine;
(b) a canister holder adapted to couple to the canister; and
(c) a valved holding chamber coupled to an end of the canister holder comprising:
(1) a housing having a first end portion, a second end portion coupled to an end portion of the canister holder, and a chamber defined in the housing, wherein a first chamber opening is defined in the first end portion and a second chamber opening is defined in the second end portion;
(2) a mouthpiece having a first end portion and a second end portion, the first end portion of the mouthpiece is coupled to the first end portion of the housing; and
(3) a valve assembly operatively coupled to the first end portion of the housing or the first end portion of the mouthpiece such that fluid flow in a first direction from the housing to the mouthpiece passes through the valve assembly defining a fluid flow path, wherein the valve assembly comprises:
(i) a conical flange having a first end portion and a second end portion, the first end portion of the conical flange is operatively coupled to the housing, or the mouthpiece; and a second end portion of the conical flange wherein the conical flange is disposed such that the conical flange tapers inwardly along a first direction extending from the first end portion of the conical flange towards the second end portion of the conical flange, and
(ii) a one-way valve element disposed at the second end portion of the conical flange, the one-way valve element being integral with the conical flange, the one-way valve element being movable to selectively permit or impede fluid flow,
wherein no portion of the valved holding chamber downstream of the housing intersects the fluid flow path perpendicularly relative to the longitudinal axis of the housing, wherein the first end portion of the mouthpiece includes a conical collar,
wherein the mouthpiece further comprises an exhaust port defined in the conical collar,
wherein the mouthpiece further comprises an exhaust valve ring disposed over the conical collar, wherein the exhaust valve ring comprises an exhaust valve element disposed over the exhaust port, and
wherein the exhaust valve ring maintains the exhaust valve element on the conical collar.

22. A valved holding chamber comprising:
(a) a housing having a first end portion, a second end portion, and a chamber defined in the housing, wherein a first chamber opening is defined in the first end portion and a second chamber opening is defined in the second end portion;
(b) a mouthpiece having a conical collar coupled to the first end portion of the housing, wherein an exhaust port is defined in the conical collar;
(c) an exhaust valve ring disposed over the conical collar, wherein the exhaust valve ring comprises an exhaust valve element disposed over the exhaust port so as to provide a one-way flow of fluid from within the mouthpiece to ambient atmosphere; and
(d) a valve assembly operatively coupled to the first end portion of the housing or the first end portion of mouthpiece such that fluid flow in a first direction from the housing to the mouthpiece passes through the valve assembly defining a fluid flow path, wherein the valve assembly comprises:
(1) a conical flange having a first end portion and a second end portion, the first portion of the conical flange is operatively coupled to the housing, or the mouthpiece, wherein the conical flange is disposed such that the conical flange tapers inwardly along a first direction extending from the first end portion of the conical flange to the second end portion of the conical flange, and
(2) a one-way valve element disposed at the second end portion of the conical flange, the one-way valve element is integral with the conical flange, the one-way valve element is movable to selectively permit or impede fluid flow.

23. A valved holding chamber comprising:
(a) a housing having a first end portion, a second end portion, and a chamber defined in the housing, wherein a first chamber opening is defined in the first end portion and a second chamber opening is defined in the second end portion;
(b) a mouthpiece having a conical collar coupled to the first end portion of the housing, wherein an exhaust port is defined in the conical collar;
(c) a one-way valve operatively coupled to the housing or the mouthpiece such that fluid flow in a first direction from the housing to the mouthpiece passes through the valve assembly; and
(d) an exhaust valve ring disposed over the conical collar, wherein the exhaust valve ring comprises an exhaust valve element disposed over the exhaust port so as to provide a one-way flow of fluid from within the mouthpiece to ambient atmosphere, and wherein the valved holding chamber further comprises a mask attached to the second end of the mouthpiece.

24. A valved holding chamber comprising:
(a) a housing having a first end portion, a second end portion, and a chamber defined in the housing, wherein a first chamber opening is defined in the first end portion and a second chamber opening is defined in the second end portion;
(b) a mouthpiece having a conical collar coupled to the first end portion of the housing, wherein an exhaust port is defined in the conical collar;
(c) a one-way valve operatively coupled to the housing or the mouthpiece such that fluid flow in a first direction from the housing to the mouthpiece passes through the valve assembly; and
(d) an exhaust valve ring disposed over the conical collar, wherein the exhaust valve ring comprises an exhaust valve element disposed over the exhaust port so as to provide a one-way flow of fluid from within the mouthpiece to ambient atmosphere, and wherein the valved holding chamber further comprises a cap adapted to selectively close the second end of the mouthpiece and a tether coupling the cap to the valve assembly.

* * * * *